US 7,331,669 B2

(12) United States Patent  (10) Patent No.: US 7,331,669 B2
Elsner  (45) Date of Patent: Feb. 19, 2008

(54) DEVICE FOR DIGITAL RETINAL IMAGING

(75) Inventor: Ann E. Elsner, Reading, MA (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 718 days.

(21) Appl. No.: 10/493,044

(22) PCT Filed: Oct. 16, 2002

(86) PCT No.: PCT/US02/32787

§ 371 (c)(1),
(2), (4) Date: Apr. 16, 2004

(87) PCT Pub. No.: WO03/039332

PCT Pub. Date: May 15, 2003

(65) Prior Publication Data

US 2004/0207811 A1    Oct. 21, 2004

Related U.S. Application Data

(60) Provisional application No. 60/350,836, filed on Jan. 22, 2002, provisional application No. 60/329,731, filed on Oct. 16, 2001.

(51) Int. Cl.
*A61B 3/14* (2006.01)
(52) U.S. Cl. .................................................. 351/206
(58) Field of Classification Search ................ 351/205, 351/206, 246
See application file for complete search history.

(56) References Cited

U.S. PATENT DOCUMENTS 4,109,237 A    8/1978  Hill ............................ 382/117
4,620,318 A    10/1986 Hill ............................ 382/117
4,729,652 A    3/1988  Effert ......................... 351/210
4,764,005 A    8/1988  Webb et al. ................. 351/205

(Continued)

OTHER PUBLICATIONS

Brakenhoff et al., "Real-Time Stereo (3D) Confocal Microscopy", Handbook of Biological Confocal Microscopy, ed. James B. Pawley, Plenum Press, New York, 1995, Chapter 21, pp. 355-362.

(Continued)

*Primary Examiner*—George Manuel
(74) *Attorney, Agent, or Firm*—Homer W. Faucett, III; Doreen J. Gridley; Ice Miller LLP

(57) ABSTRACT

A portable, lightweight digital imaging device uses a slit scanning arrangement to obtain an image of the eye, in particular the retina. The scanning arrangement reduces the amount of target area illuminated at a time, thereby reducing the amount of unwanted light scatter and providing a higher contrast image. A detection arrangement receives the light remitted from the retinal plane and produces an image. The device is operable under battery power and ambient light conditions, such as outdoor or room lighting. The device is noncontact and does not require that the pupil of the eye be dilated with drops. The device can be used by personnel who do not have specialized training in the eye, such as emergency personnel, pediatricians, or general practitioners. Images can be viewed in the device or transmitted to a remote location. The device can also be used to provide images of the anterior segment of the eye or other small structures.

82 Claims, 7 Drawing Sheets

U.S. PATENT DOCUMENTS

| | | | | |
|---|---|---|---|---|
| 4,768,873 | A | 9/1988 | Webb | 351/205 |
| 4,768,874 | A | 9/1988 | Webb et al. | 351/206 |
| 4,838,679 | A * | 6/1989 | Bille | 351/205 |
| 4,923,297 | A | 5/1990 | Arndt | 351/208 |
| 5,028,802 | A | 7/1991 | Webb et al. | 250/571 |
| 5,303,709 | A | 4/1994 | Dreher et al. | 600/476 |
| 5,309,339 | A | 5/1994 | Webb | 362/259 |
| 5,532,771 | A | 7/1996 | Johnson et al. | 351/211 |
| 5,563,710 | A | 10/1996 | Webb et al. | 356/445 |
| 5,673,097 | A | 9/1997 | Heacock | 351/218 |
| 5,784,148 | A | 7/1998 | Heacock | 351/221 |
| 5,787,890 | A | 8/1998 | Reiter et al. | 600/476 |
| 5,815,242 | A | 9/1998 | Anderson et al. | 351/221 |
| 5,861,938 | A | 1/1999 | Heacock | 351/218 |
| 5,867,251 | A | 2/1999 | Webb | 351/221 |
| 5,949,520 | A | 9/1999 | Heacock | 351/221 |
| 6,094,269 | A | 7/2000 | Ben-Dove et al. | 356/623 |
| 6,099,125 | A | 8/2000 | Webb et al. | 351/211 |
| 6,112,114 | A | 8/2000 | Dreher | 600/476 |
| 6,236,877 | B1 | 5/2001 | Elsner et al. | 600/407 |
| 2002/0101566 | A1 | 8/2002 | Elsner et al. | 351/200 |

OTHER PUBLICATIONS

Elsner et al., "Infrafred Imaging of Sub-retinal Structures in the Human Ocular Fundus", *Vision Res.*, 1995, vol. 36, No. 1, pp. 191-205.

Elsner et al., "Reflectometry with a scanning laser ophthalmoscope", *Applied Optics*, Jul. 1, 1992, vol. 31, No. 19, pp. 3697-3710.

Koester et al. "Optical sectioning with the scanning slit confocal microscope: applications in opthalmology and ear research", *SPIE*, vol. 1161: *New Methods in Microscopy and Low Light Imaging* (1989), pp. 378-388.

Plesch et al., "Optical characteristics of a scanning laser ophthalmoscope", *SPIE*, vol. 1161: *New Methods in Microscopy and Low Light Imaging* (1989), pp. 390-398.

Zhang et al., "Feature-bit-plane matching technique for estimation of motion vectors", *Electronic Letters*, May 28, 1998, vol. 34, No. 11, pp. 1087-1089.

Zinser et al., "Confocal Laser Tomographic Scanning of the Eye", *SPIE*, vol. 1161: *New Methods in Microscopy and Low Light Imaging* (1989), pp. 337-339.

Ashman et al., "Improvement in Colour Fundus Imaging Using Scanning Laser Opthalmoscopy", *Lasers Med Sci* 2001, 16:52-59.

Bennett et al., No Title, Letters to the Editor, No Publication Title, No Date, No Pages.

Elsner et al., "Photopigment Densitometry with a Scanning Laser Ophthalmoscope," *Opt. Soc. Am. Technical DigestI*, 11, 122, 1988.

Elsner et al., "Retinal Light Scattering," *J. Opt. Soc. Amer. Technical Digest*, 15, 5, 1990 (summary).

Samples et al., "Use of the Infrared Fundus Reflection for an Identification Device", *American Journal of Opthalmology*, Nov. 1984 vol. 98, No. 5, pp. 636-637.

Smith, Redmond., "Video laser ophthalmoscopy in diabetes", , Editorial, *British Journal of Ophthalmology*, 1991, 75, p. 513.

Beausencourt et al., "Quantitative Analysis of Macular Holes with Scanning Laser Tomography," *Ophthalmology*, vol. 104, No. 12, Dec. 1997, pp. 2018-2029.

Burns et al., "Cone Photoreceptor Directionality and the Optical Density of the Cone Photopigments," Vision Science and its Applications, 1996 Technical Digest Series vol. 1, Optical Society of America, pp. 96-99.

Elsner et al. "Changes in fundus pathology measurements with wavelength in the near IR,", Annual Meeting of the Optical Society Technical Digest, 10, 88, 1992, abstract.

Elsner et al., "Advantages of Infrared Imaging in Detecting Choroidal New Vessels," Vision Science and its Applications, 1995 Technical Digest Series vol. 1, Optical Society of America, pp. 192-195.

Elsner et al., "Diagnostic Applications of Near Infrared Solid-State Lasers in the Eye," IEEE Lasers and Electro-Optics Society 1994 7th Annual Meeting 1994, Conf. Proceedings, vol. 1, pp. 14-15.

Elsner et al., "Evaluating the Photoreceptor/RPE Complex with an SLO," Noninvasive Assessment of the Visual System, Technical Digest Series, Optical Society of America, vol. 3, Conf. Ed., 1990, pp. 40-43.

Elsner et al., "Imagining retinal and subretinal structures with near infrared light," Annual Meeting of the Optical Society of America, 17, 103, 1991, abstract.

Elsner et al., "Infrared Imaging in Age-Related Macular Degeneration: Retinal Pigment Epithelial Detachments," Ophthalmic and Visual Optics, Noninvasive Assessment of the Visual System, 1993 Technical Digest Series vol. 3, Optical Society of America, pp. 282-285.

Elsner et al., "Infrared Imaging of Sub-Retinal Structures in the Human Ocular Fundus," *Vision Res.*, vol. 36, No. 1, pp. 191-205, 1996.

Elsner et al., "New Devices for Retinal Imaging and Functional Evaluation," Ch. 2 of Practical Atlas of Retinal Disease and Therapy, 2nd ed., ed. William R. Freeman, Philadelphia 1997, pp. 19-55.

Elsner et al., "Photopigment Concentration in Normal and Photocoagulated Human Tissue", *Invest Ophthalmol. Vis. Sci.*, Suppl. 30, 370, 1989, p. 15.

Elsner et al., "Quantitative Reflectometry with the SLO," Laser Scanning Ophthalmoscopy and Tomography, ed. J.E. Nasemann & R.O.W. Burk, Quintessenzverlag, 1990, pp. 109-121.

Elsner et al., "Reflectometry in Retinal Tears and Detachments," *Clin. Vision Sci.*, vol. 7, No. 6, 1992, pp. 489-500.

Elsner et al., "Reflectometry with a scanning laser ophthalmoscope," *Applied Optics*, Jul. 1, 1992, vol. 31, No. 19, pp. 3697-3710.

Elsner et al., New Views of the Retina/RPE Complex: Quantifying Sub-retinal Pathology, Noninvasive Assessment of the Visual System, Technical Digest Series, Optical Soc. Of Amer., vol. 1, 1991, pp. 150-153.

Elsner, A., "Scanning Laser Ophthalmoscopy, Tomography, and Visual Function Evaluation," Editorial Minireview, *Clin. Vision Sci.*, vol. 7, No. 6, pp. V-viii, 1992.

Elsner et al., "Detecting AMD with Multiply Scattered Light Tomography," *International Ophthalmology*, 23:245-250, 2001.

Elsner et al., "Foveal Cone Photopigment Distribution: Small Alterations Associated With Macular Pigment Distribution", Investigative Ophthalmology & Visual Science, Nov. 1998, vol. 39, No. 12, pp. 2394-2404.

Elsner et al., "Multiply scattered light tomography and confocal imaging: detecting neovascularization in age-related macular degeneration," Optics Express, vol. 7, No. 2, Jul. 17, 2000, pp. 95-106.

Elsner et al., "Multiply scattered light tomography: Vertical Cavity Surface Emitting laser Array Used for Imaging Subretinal Structures," *Lasers and Light in Ophthalmology*, 8(0), 1998, pp. 1-10.

Elsner et al., "Scattering laser reflectometry of retinal and subretinal tissues," Optics Express, vol. 6, No. 13, Jun. 19, 2000, pp. 243-250.

Hartnett et al., "Deep Retinal Vascular Anomalous Complexes In Advanced Age-Related Macular Degeneration", Ophthalmology, vol. 103, No. 12, Dec. 1996, pp. 2042-2053.

Harnett et al., "Characteristics of Exudative Age-Related Macular Degeneration Determined In Vivo With Confocal and Indirect Infrared Imaging", Opthalmology, vol. 103, No. 1, Jan. 1996, pp. 58-71.

Miura et al., "Grading of Infrared Confocal Scanning Laser Tomography and Video Displays of Digitized Color Slides in Exudative Age-Related Macular Degeneration," RETINA 22:300-308, 2002.

Van Norren et al., "A Continuously Recording Retinal Densitometer", Vision Research, vol. 21, 1981, pp. 897-905.

* cited by examiner

DEVICE FOR DIGITAL RETINAL IMAGING

CROSS REFERENCE TO RELATED APPLICATIONS

This application claims priority under 35 U.S.C. 119(e) of U.S. Provisional Application No. 60/350,836, filed on Jan. 22, 2002, and U.S. Provisional Application No. 60/329,731, filed on Oct. 16, 2001, the disclosures of both of which are incorporated by reference herein.

STATEMENT REGARDING FEDERALLY SPONSORED RESEARCH OR DEVELOPMENT

The work leading to the invention received support from the United States federal government under Department of Defense Low Vision Grant No. DAMD-17-01-2-0032. The federal government may have certain rights in this invention.

BACKGROUND OF THE INVENTION

The human retina is susceptible to damage from a variety of environmental factors, including laser light impact and other trauma, as well as disease. Once damaged, the cells responsible for capturing light energy and transducing it into a neural signal, the photoreceptors, do not regenerate. In fact, none of the neural cells of the retina can yet be made to readily regrow in the adult human. When damage is severe enough, there is permanent vision loss in an area. Healthy photoreceptors do not migrate long distances toward the damaged area to replace damaged ones.

If the affected region is in the central macula, known as the fovea, then the ability to see fine detail, read at rapid rates, or recognize objects at great distances may be lost. The peripheral areas of vision do not have sufficient sampling density to perform these tasks to the same degree. Thus, early detection and treatment of potentially sight-robbing damage are crucial in maintaining central vision.

One of the chief problems in early detection has been the difficulty of imaging damage to a small area of retina. The macula presents a small target, 6000 microns. The portion that is necessary for seeing damage that precludes observation of fine detail and reading is even smaller, about 600 microns. To examine this latter portion properly, it would be desirable to image the central 20 degrees of the macula with sufficient magnification and contrast to determine whether an individual is at risk for permanent vision loss.

The ophthalmoscope or fundus camera has been used to view and image the retina. Originally, these devices flooded the retina with white light. Subsequent devices have used selective wavelengths that have been found suitable for viewing or imaging particular structures or contrast between structures.

Flood illumination produces images of the retina that often are subject to poor contrast due to the long range scatter not only from out of plane tissues, but also from the biological tissues that are inherently scattering, especially those within and near the retina. Scanning of an illumination source is a well-known method to increase the contrast in images by reducing unwanted scatter. Webb et al. disclose double scanning optical apparati that scan both incident and reflected light using a horizontal scanning element, such as a rotating multifaceted polygonal reflector, and a vertical scanning element, such as a reflecting galvonometer. The instrument is able to provide a two-dimensional output representative of reflection characteristics of the eye fundus. See U.S. Pat. Nos. 4,768,873 and 4,764,005. Webb et al. disclose a laser scanning ophthalmoscope in which a line beam is scanned across an eye. See U.S. Pat. No. 4,768,874.

Reflectometry techniques with a scanning laser ophthalmoscope (SLO) have been described by Elsner et al. See, for example, Elsner A. E., et al., Reflectometry with a scanning laser ophthalmoscope, *Applied Optics*, Vol. 31, No. 19 (July 1992), pp. 3697-3710. The SLO is advantageous for reflectometry, i.e. quantitative imaging, in that a spot illumination is scanned in a raster pattern over the fundus, improving image contrast significantly over flood illumination. Unwanted scattered light can be further rejected by using confocal apertures. The aperture may be a circle of variable diameter or annular, depending on the desired mode. The desired light is transmitted to a detector.

The extensive use of near infrared light as an illumination source, in lieu of other wavelengths or color images, is further discussed in Elsner, A. E., et al., Infrared Imaging of Sub-retinal Structures in the Human Ocular Fundus, *Vision Res.*, Vol. 36, No. 1 (1996), pp. 191-205; Elsner, A. E., et al., Multiply scattered light tomography: Vertical cavity surface emitting laser array used for imaging subretinal structures, *Lasers and Light in Ophthalmology*, 1998; Hartnett, M. E. and Elsner, A. E., Characteristics of Exudative Age-related Macular Degeneration Determined In Vivo with Confocal and Indirect Infrared Imaging, *Ophthalmology*, Vol. 103, No. 1 (January 1996), pp. 58-71; and Hartnett, M. E., et al., Deep Retinal Vascular Anomalous Complexes in Advanced Age-related Macular Degeneration, *Ophthalmology*, Vol. 103, No. 12 (December 1996), pp. 2042-2053. Infrared imaging with a scanning laser ophthalmoscope (SLO) has been used to perform reflectometry techniques to view the eye rapidly and noninvasively. Once implemented with scanning laser devices, infrared and near infrared imaging of sub-retinal structure in the ocular fundus has been able to reveal sub-retinal deposits, the optic nerve head, retinal vessels, choroidal vessels, fluid accumulation, hyperpigmentation, atrophy, and breaks in Bruch's membrane. Infrared light is absorbed less than visible light and may scatter over longer distances. With flood illumination, these features have not been observed with the same clarity or in lesser numbers. The relatively less absorption has advantages in that a minimum of light may be used as an illumination source. However, the reflected and scattered light must be separated in some manner, and the light used to accentuate the features of interest made available to the user.

The methods for detecting and localizing such features are described in the prior art of the inventor and colleagues: Elsner, A. E., et al., Infrared Imaging of Sub-retinal Structures in the Human Ocular Fundus, *Vision Res.*, Vol. 36, No. 1 (1996), pp. 191-205; Elsner, A. E., et al., Multiply scattered light tomography: Vertical cavity surface emitting laser array used for imaging subretinal structures, *Lasers and Light in Ophthalmology*, (1998); Elsner, A. E., et al., Foveal Cone Photopigment Distribution: Small Alterations Associated with Macular Pigment Distribution, *Investigative Ophthalmology & Visual Science*, Vol. 39, No. 12 (November 1998), pp. 2394-2404; Hartnett, M. E. and Elsner, A. E., Characteristics of Exudative Age-related Macular Degeneration Determined In Vivo with Confocal and Indirect Infrared Imaging, *Ophthalmology*, Vol. 103, No. 1 (January 1996), pp. 58-71; and Hartnett, M. E., et al., Deep Retinal Vascular Anomalous Complexes in Advanced Age-related Macular Degeneration, *Ophthalmology*, Vol. 103, No. 12 (December 1996), pp. 2042-2053, as examples. Specifically, when a retinal image acquired is only of the macula, centered on the fovea, the only features present with near infrared illumination are the normal retinal and choroidal blood vessels, and potentially superficial reflections, such as from the fovea. In a monochromatic image, any differences from these features in image intensity, beyond the noise inherent in any electronic signal, is interpreted as pathology. If the optic nerve head is also in the image, either due to a sufficiently large field of view or positioning of the eye with respect to the instrument to incorporate this feature, then intensity changes in the retina also define the position and condition of such a structure. It has been shown by Hartnett and Elsner, 1996, and Miura et al, 2002, that such monochrome images using infrared illumination are superior for the detection of certain features over methods using color photography. Hartnett, M. E. and Elsner, A. E., Characteristics of Exudative Age-related Macular Degeneration Determined In Vivo with Confocal and Indirect Infrared Imaging, *Ophthalmology*, Vol. 103, No. 1 (January 1996), pp. 58-71; Miura, M., et al., Grading of Infrared Confocal Scanning Laser Tomography and Video Displays of Digitized Color Slides in Exudative Age-Related Macular Degeneration, *Retina*, Vol. 22, No. 3 (2002), pp. 300-308. No modestly priced, simple to use instrument is available that operates using this method.

Current prior art retinal imaging instruments use a photodiode, a photomultiplier tube, or other spot detector, i.e. single point detection. In previously published retinal imaging devices, single spot detectors have been placed optically in the retinal plane in the instruments above (Webb, as above) or the pupil plane (van Norren). Norren, D. and J. van der Kraats, A continuously recording retinal densitometer, *Vision Research* 21 (1981), pp. 897-905. Koester et al. have described a confocal microscope using a slit scanning system in studying the corneal endothelial cell layer of the eye, as well as the ear. Koester, C. J., et al., Optical sectioning with the scanning slit confocal microscope: applications in ophthalmology and ear research, *SPIE: New Methods in Microscopy and Low Light Imaging*, Vol. 1161 (1989), pp. 378-388. Koester, C. J., Scanning mirror microscope with optical sectioning characteristics: applications in ophthalmology, *APPLIED OPTICS*, Vol. 19, No. 11 (1 Jun. 1980), pp. 1749-1757.

A scanning laser ophthalmoscope is a large, expensive piece of equipment intended for use by ophthalmologists or other eye specialists in their offices or laboratories. Equipment of this nature is not suitable for use by non-specialists or emergency personnel in the field. To date, alternating current power sources and complex synchronization circuitry have been necessary to produce and acquire images, and control or ancillary computer systems are typically necessary. This presents a problem with weight, footprint, and power. European and US configurations have had to be designed in, due to 110 as opposed to 220 V power, and 60 as opposed to 50 Hz. Further, the video standards differ from country to country, so that video rate imaging has been made more difficult and cumbersome by requiring two sets of circuitry. Personnel in the field rely on either an ophthalmoscope or fundus camera instrumentation to obtain a view of the human retina. Both direct and indirect ophthalmoscopes require considerable skill to obtain a view of the macula of each eye, often not possessed by medical personnel not trained in an eye subspecialty. These images are not seen by anyone remote from the patient, and therefore a description by unskilled personnel is often the only data available to be transferred to an expert located elsewhere. Direct and indirect ophthalmoscopes do not produce images that can be stored and examined at another time or location. Fundus camera devices do provide film or digital storage of the area examined; however, fundus camera devices using flood illumination of a wide area of the retina often fail to produce images of high contrast. Untrained personnel often do not produce high quality results. The quality of the image of the retina from both fundus cameras and ophthalmoscopes depends upon the diameter of the pupil, with a large diameter pupil needed for acceptable images in the indirect ophthalmoscope and many fundus cameras. Non-mydriatic fundus cameras, requiring little or no dilation, depend upon flashed illumination and relatively expensive, high sensitivity detector arrays to obtain an image. These devices use flood illumination and do not depend upon the light efficiency of a scanning design, and therefore typically operate using uncomfortably bright lights that lead to pupil constriction in eyes not having received dilatation medication.

Those instruments developed commercially to date for digital imaging of the retina require computer systems for operation, including proprietary software. There is considerable training needed by the non-expert to be able to operate such a device. There is often a high degree of computer skill needed to acquire and transmit the image data from these devices. The data are often stored in proprietary file formats or require image storage, processing, or transmission methods that require additional software, which may not be compatible with other patient data. Additional training is necessary to interpret these images, or the data from them, often requiring consultation time and travel of an individual to the site of the instrument for training.

Current imaging devices are not readily suited for use with personal digital assistants, wireless transmission, or the ubiquitous storage devices used with consumer digital cameras. Such images, when using proprietary software or file formats, are not readily transferred and used with laptop or other computers in a shared environment.

SUMMARY OF THE INVENTION

The present invention relates to a device designed as an "eye sensor" for general use, achieving simplicity of operation, patient comfort, and low power requirements. The device is small, lightweight, and portable and presents a high contrast image. The device is suitable for providing triage for trauma and can readily interface with modern computer technology for remote or telemedicine applications. The device is able to operate in extreme heat or cold, when wet, while on a moving surface, and in a cordless mode. The device can be manufactured relatively inexpensively at significantly less cost than conventional scanning laser ophthalmoscopes.

The device includes an illumination source, a scanning arrangement, a detection arrangement, a beam separation arrangement, and a controller. The scanning arrangement is disposed on an illumination path from the illumination source to a target and is operative to scan light passed through a slit in the illumination path across a desired focal plane of the target, e.g., the retinal plane, through an entrance more narrow than the desired focal plane, e.g., the pupil. The detection arrangement is disposed to receive light remitted from the target and operative to produce an image. The beam separation arrangement is disposed on a return path from the target separated from the illumination path and is operative to receive light remitted from the target and to direct remitted light on a detection path to the detection arrangement. The beam separation arrangement is configured to space the illumination path and the return path sufficiently apart to reduce reflections from sources out of the desired focal plane and sufficiently closely to obtain an image of a sufficient desired resolution. The controller is in communication with the illumination source, the scanning arrangement, and the detection arrangement.

The device differs from instruments currently on the market in that it features scanning of one or more light sources, one of which is preferably near infrared, at a fraction of the cost of high end devices. The device can have on board digital memory or another storage device, such as is used in a digital camera. The instrument is stand-alone; in the preferred embodiment, a personal computer is not required to operate the device. The data can be transmitted to a computer, memory device, or other device including via wireless broadcast. A laptop and consumer grade software are all that is necessary to access the images in cases in which a computer is used.

The device is minimized in weight or mass and is portable, so that it is suitable for use outside of specialized ophthalmological offices and laboratories. Moving parts are eliminated or minimized, particularly those that require power to operate. The device can operate solely on batteries. The device can be motorized for remote access, using either DC operation or AC operation, as power supplies permit. The device can be made to draw its power though a single cable, such as to a computer. The computer can be a laptop, which is consistent with use as a portable device.

DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
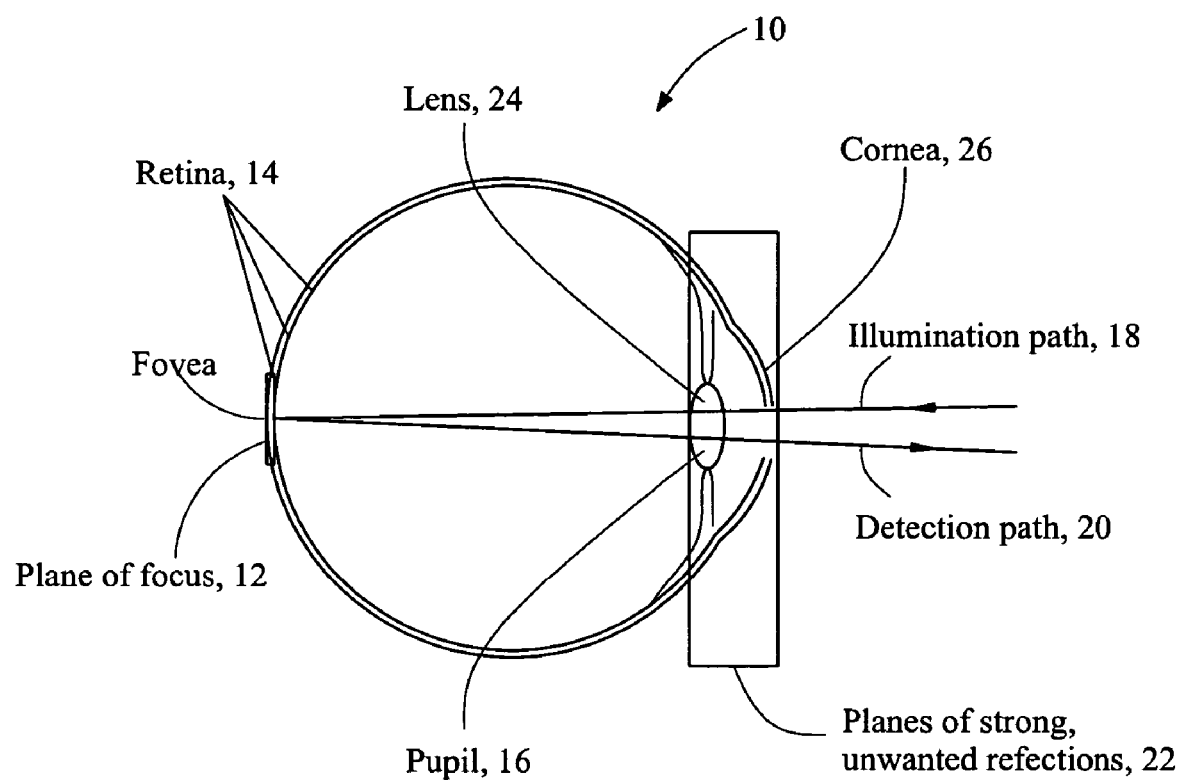
FIG. 1 is a schematic diagram of an eye showing selected tissues and the retinal plane as a target focal plane as distinguished from the highly reflective and more anterior optical planes.

The present invention relates to a small, portable lightweight instrument or device of low cost particularly suitable for examining the retinal and subretinal layers of the eye 10 (see FIG. 1) for abnormalities. The device is noncontact and does not require drops to dilate the pupil of the eye. Referring to FIG. 1, the plane of focus 12 of the device for the retina 14 is that with the greatest amount of light return. When a human retina is imaged, light from an illumination source is passed through a slit to produce a line source and scanned across a desired focal plane in the eye after passing through the entrance pupil 16 of the eye, which is narrower than the focal plane of interest. Light enters through one or more portions of the pupil (see exemplary illumination path 18) and is remitted and collected through primarily other portions (see exemplary detection path 20), which minimizes the collection of unwanted light that is reflected from other planes 22, such as the lens 24 and cornea 26, that would be on the same optical axis if the illumination and detection pathways were coincident. Slit scanning of the illumination onto the target, discussed further below, reduces the amount of target area illuminated at a time, thereby reducing the amount of unwanted scatter from both nearby and distant structures, which are not illuminated simultaneously with the light illuminated by the slit. This provides a higher contrast image. The light from the desired focal plane is collected and stored digitally in electronic or magnetic form and/or transmitted to a remote site if needed. The footprint of the optical components can be minimized and the device is operable by DC battery power. The main controls are few and simple, primarily a power switch, a focusing mechanism, and a mechanism to increase or decrease the light level of the illumination source.

Figure 2:
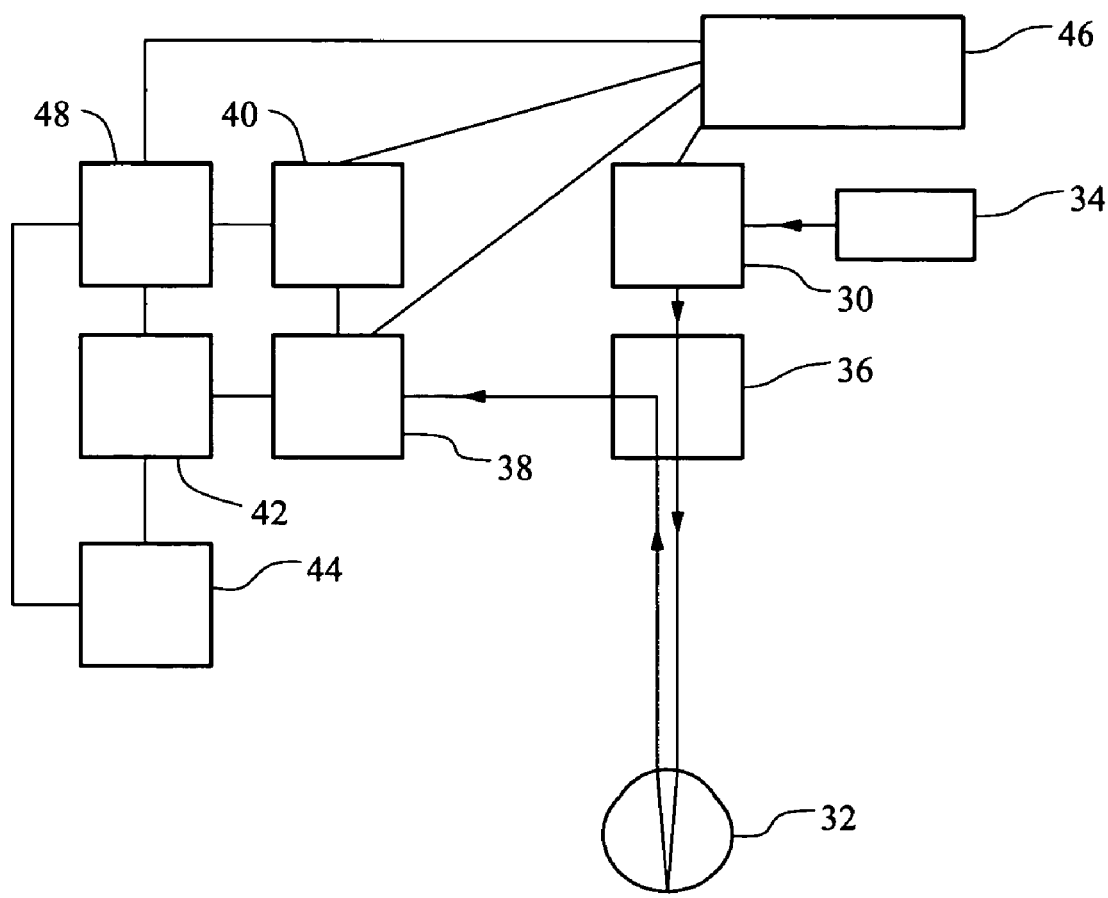
FIG. 2 is a schematic diagram of an optical imaging system generally according to the present invention.

FIG. 2 depicts generally an optical imaging system according to the present invention. One or more scanning elements 30 direct the light to and, in some embodiments, from a target 32 to decrease the unwanted scattered light that would result with flood illumination. This system includes an illumination source and beam shaping optics, illustrated collectively at 34, for directing incident light at the scanning element 30, which then directs the light through a beam separation element 36, then at the target 32. The intended target for the present device is within the eye, although the device can be used with other targets. An illuminated portion on the target 32 remits light via a beam separation element 36 to components along a detection pathway, illustrated schematically at 38, where an image of the target is formed, and light energy is changed to electrical or magnetic energy, for purposes of image capture or image storage. This image is then shown on a display 40 and/or stored on a storage device 42 in communication with the components on the detection pathway 38. The image can additionally or alternatively be transmitted either by storage media, cables, or wireless communication to a database 48 or to a display, computer, personal digital assistant, or other digital or analog device 44 for the purposes of examining the target 32.

Control electronics or mechanical adjustments, illustrated schematically at 46, allow the end user to control the illumination source 34, the scanning element 30, the detection pathway components 38, the display 40, and the database 48, as well as devices such as alignment or focusing monitors, synchronization circuitry, transmission using wires or wireless methods, additional image monitors, image capture or recording devices, and image storage devices that are interconnected with them. These resulting images can be fed into the database of image data 48, or used without reference to the database. The database of images 48 may be used via components 44 for telemedicine, training, and distance education concerning the status or health of the target, as the user of this instrument may be remote from a decision maker or may be unskilled in the arts of image acquisition or image interpretation of this type of image. The database can also contain normative, classification, or quantitative data and decision-making procedures concerning the outcome of the data.

The separation element 36 can be any type of separation element, such as a beam splitter with the reflective portion intersecting the beam of light and directing it towards target 32, while the more transmissive portion passes the light toward the detection pathway 38, shown schematically in FIG. 2. The beam separator can also work such that the transmissive portion intersects the beam of light directed towards the target, but reflects the light returning from the target. A beam separator that permits only a minimal amount of spatial overlap between the light directed towards the target 32 and the light remitted from the target, and similarly the entrance pupil to the target, provides the benefit of minimizing the collection of light from reflective surfaces that are not in the plane of the target. When the human eye is the target 32, the light enters in one or more portions of the pupil of the eye, and is remitted and collected from primarily other portions of the pupil, as discussed above in conjunction with FIG. 1. The beam separator 36 can have one or more reflective or transmissive portions. These reflective and transmissive portions can be made of reflectors of a relatively permanent nature, or can be made of elements that separate the beams by means of polarization properties of the light directed towards and away from the target. With a mirror beam splitter, the light entering the eye can have the greater loss of transmission through the beam splitter, to preserve more of the light returning from the eye. The beam separator can be controlled by known electro-optic devices such as LCD, spatial light modulator, or polarizing elements. With a polarizing beam splitter, additional polarization elements can be used to reduce unwanted reflections from the anterior segment. The beam separator can use elements positioned mechanically, thereby controlling the position or amount of the light towards or away from the target. The beam separator can contain reflective or transmissive elements that are only partially reflective, such as a 90/10 beam splitter. When the target is the human eye, the preferred embodiment includes a separation element that can make use of a small and powerful illumination source 34, with a relatively lesser return from the eye.

Figure 3:
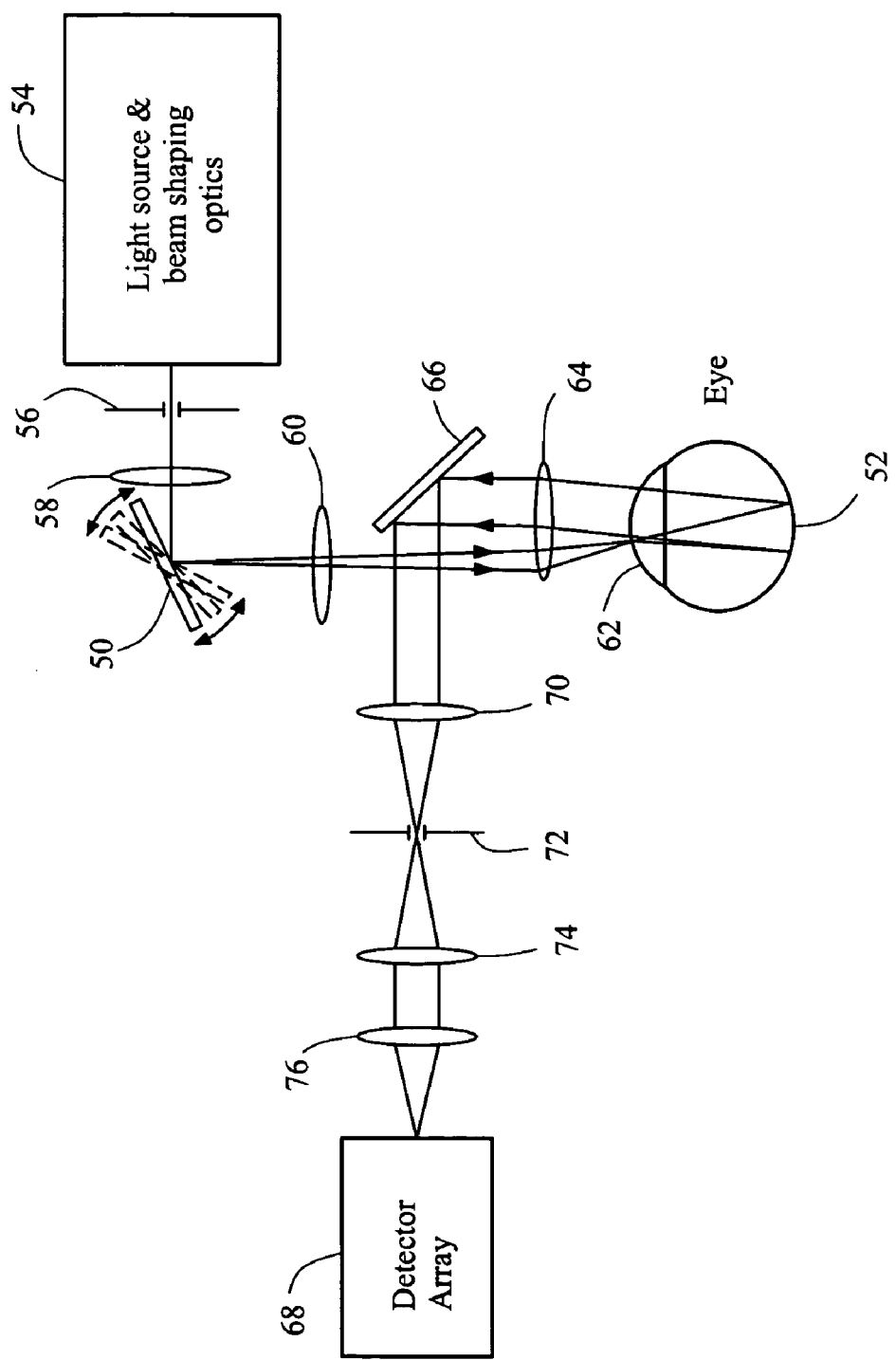
FIG. 3 is a schematic diagram illustrating an embodiment of the optical imaging system of the present invention incorporating one scanning element.

FIG. 3 illustrates an embodiment, which describes a group of configurations, in which there is a single scanning element 50 that directs the light to a target 52 but not the light remitted from the target 52. The light from an illumination source 54 undergoes beam shaping and is brought to a focus in a plane conjugate with the target 52 at a slit 56. The slit is illustrated in more detail in FIG. 5. (In FIGS. 3 and 4, the slit has a long axis orthogonal to the plane of the figure.) In FIG. 3, the light passing through the slit 56 is directed by a focusing element 58 onto the scanning element 50, which rotates or oscillates to reflect the light sequentially across the target in a direction perpendicular to the long axis of the slit 56. From the scanning element 50 the light is then directed by one or more focusing elements 60, through a narrow angle of entrance, e.g., the pupil 62, to a focus at the target 52, e.g., the retinal plane. (In FIG. 3, the entrance and focal planes are illustrated schematically only; see FIG. 1 for greater detail.) The light at slit 56 is in an optical plane conjugate to the target 52. The light at scanning element 50 is in an optical plane conjugate with the plane of the narrow angle of entrance 62. A focusing element 64 is preferably mounted for movement in an axial direction to allow focusing of the light on the target 52.

As noted above, scanning the light across the target through a slit (and scanning again in the detection pathway, described further below) aids in decreasing unwanted scattered light in the resulting image. The scanning can be accomplished in a variety of ways. For example, a mirror component may be mounted to a rotating or oscillating element, a magnetic device, a spring, a torsion rod, or other mechanically controlled device such as a solenoid, or a gravity controlled device. The scanning element can be activated in any suitable manner, such as by a button or lever press, a sliding switch, a toggle switch, or a knob rotation by the operator. The scanning element is preferably driven by a battery operated DC motor, which is an inexpensive configuration and allows the device to be portable.

Light returning from the target 52 is separated from light striking the target at beam separation element 66. In the embodiment shown in FIG. 3, the separation element is illustrated as a mirror that does not intersect the light directed towards the target 52 on the illumination pathway. The mirror is located on the return pathway to intersect and thereby reflect the light remitted from the target 52 on the detection pathway to a detector array 68. The separation element 66 can also be a beam splitter with the reflective portion intersecting the beam of light directed at the target 52, with the transmissive portion directing light remitted from the target, or any other combination of elements as described concerning FIG. 2 above to separate the light from the illumination pathway from that remitted from the target 52 and direct the remitted light towards the detection pathway. By spatially separating the light directed towards the target 52 from the light returning from the target, unwanted, direct reflections from focal planes not in the plane of the target can be eliminated by minimizing the spatial overlap at beam separator 66. With respect to the target, the illumination is directed at the target from a slightly different position than is the detection pathway from the remitted light, so that there is minimal spatial overlap between the detection and illumination pathways, thereby minimizing any unwanted reflections of optical elements, including those often found in association with the target such as the cornea and lens of the human eye when the retina is the target (see FIG. 1).

The separation element 66 can be a partially or fully reflective surface that does not intersect the light directed towards the target 52. The reflective surface can be a mirror or a beam splitter with the reflective portion not intersecting the beam of light directed at the target, as shown. The separation element can also be any number of other separation elements, such as a beam splitter with a reflective portion intersecting the beam of light directed towards target and a transmissive portion including a mirror that reflects less than 100% of the light towards the target or a transmissive portion intersecting the beam of light directed towards the target and the reflective portion allowing the light from the target to pass.

Further decrease of light from unwanted planes can be obtained by directing the light on the detection pathway from the target 52 through focusing element(s) 70 and passing it through an aperture 72, which is in an optical plane conjugate to the target 52. The light then passes through focusing elements 74 and 76, and forms an image on a two-dimensional detector array 68. The detector array can be a CCD, CMOS, video camera, or other array that changes light energy into electronic or magnetic energy for image acquisition and/or display.

Figure 4:
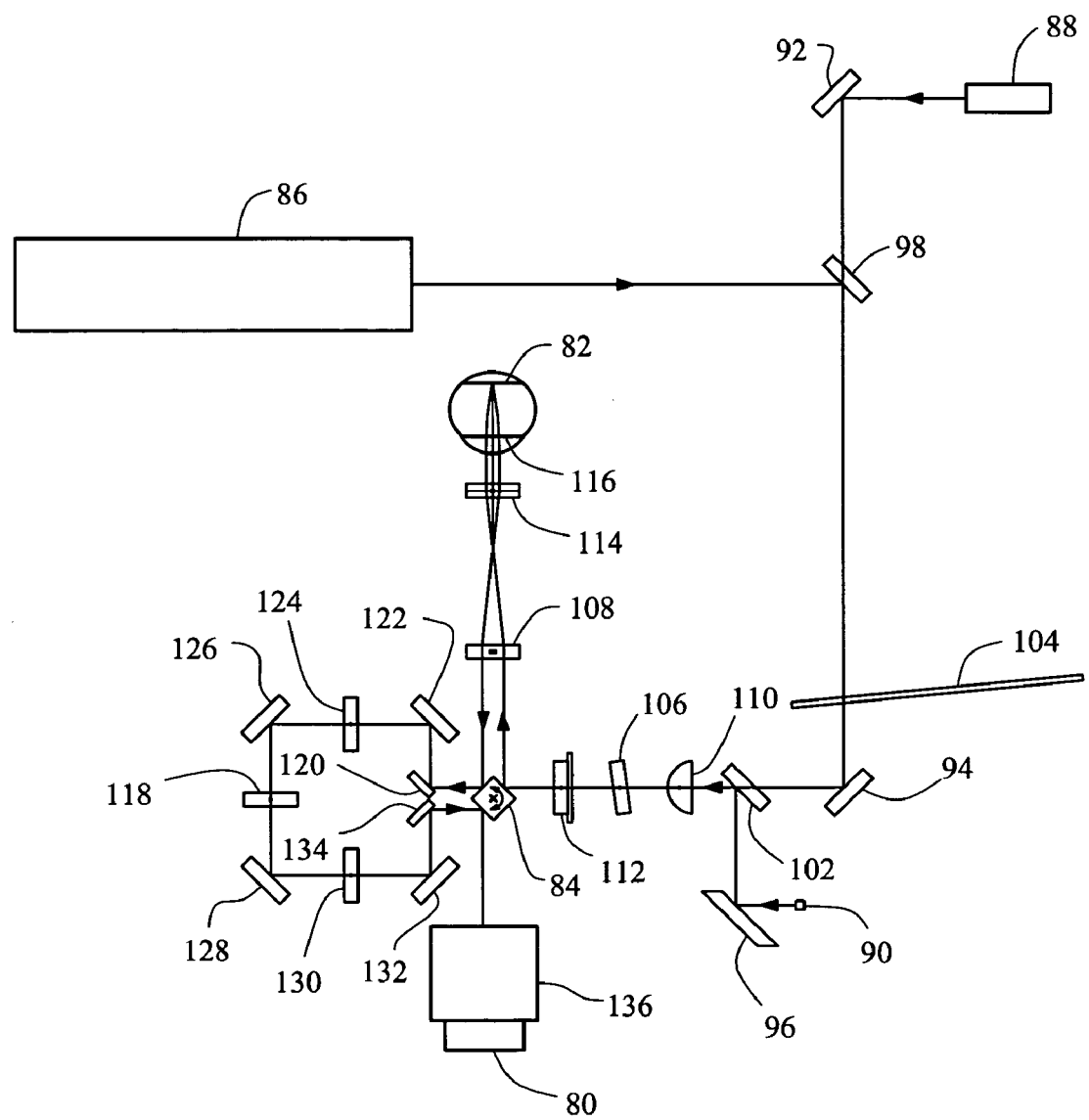
FIG. 4 is a schematic diagram illustrating an embodiment of the optical imaging system of the present invention incorporating one scanning element and three instances of scanning utilizing three portions of the element.

FIG. 4 depicts a further embodiment of an optical imaging system according to the present invention. This system includes the basic elements discussed in conjunction with FIGS. 1 and 2, in which light from a source is directed via a scanning element to a target and returned to a detection pathway, the illumination and return light being separated by a separation element. In the embodiment of FIG. 4, light from the illumination source is scanned three times prior to reaching a detector array 80. A first scan is in the illumination pathway prior to the target 82. The next two scans are in the detection pathway from the separation element to the detector 80. In the embodiment of FIG. 4, a scanning element 84 is illustrated as a rotating cube with four reflective surfaces. The first scan is done using a face of the scanning element 84 in a first disposition, and the next two scans are done using faces of the scanning element in other dispositions, all dispositions being in approximately optically conjugate planes with the entrance pupil. In this embodiment, the scanning element 84 also functions as the separation element to the detection pathway.

The embodiment depicted in FIG. 4 includes illumination sources 86, 88, and 90 for directing incident light at the target 82. Imaging can be performed with a device having one, two, three, or more such sources, with each source differing to provide unique and beneficial properties, such as a different wavelength, increased power, or different polarization properties. All illumination sources can be controlled by the control electronics 46 (see FIG. 2), for example, to turn on and off, to operate in a steady state mode or a flash mode, or to control intensity of the light, as discussed further below. The light from each illumination source can undergo beam shaping prior to being directed towards additional elements in the optical imaging system.

The light from the illumination sources can be directed with turning mirrors 92, 94, and 96, and then combined into a single beam with beam combining elements 98 and 102. These elements can be reflective and transmissive elements; can be dichroic mirrors to take advantage of the wavelength differences of the illumination sources 86, 88, and 90; or they can reflect or transmit according to polarization properties of the illumination sources 86, 88, and 90. As the light is combined, the preferred embodiment is to combine each of the illumination sources to the next by a pair of beam combining elements: a first element, such as a mirror, to steer and a second element to combine two beams and further steer one or the other beam. In the illustrated preferred embodiment, light from illumination source 90 is combined with the main beam from sources 86 and 88 by turning mirror 96 and beam combining element 102. The position of the combining elements can be configured to minimize the space taken by the device, rather than configured for ease of optical alignment.

Figure 5:
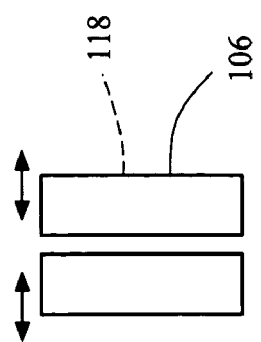
FIG. 5 is a schematic diagram illustrating an embodiment of a slit in the illumination pathway to control the extent or intensity of the illumination light, and also illustrating a confocal aperture in the detection pathway to limit sampling prior to the detector to light primarily in the plane of focus of a target in a conjugate optical plane.

The intensity of the light from the sources may be controlled in any suitable manner if desired, such as to decrease the level down from the FDA approved level for existing prior art for continuous viewing. For example, in FIG. 4, the light from the illumination sources 86 and 88 is controlled by an intensity control element 104, which may be an optical element, such as a neutral density filter. The intensity of the light can also be controlled mechanically, in which case slit 56 in FIG. 3 or 106 in FIG. 4 represents an adjustable slit or iris diaphragm that may be controlled mechanically. (For example, when the element in FIG. 5 represents the slit in the illumination pathway, the width of the slit may be increased or decreased as illustrated by the arrows.) The illumination control device may thus be operated mechanically or electronically, such as with a finger operated screw. The intensity of the light can also be increased or decreased with a polarizing element in a position depicted by 104 in FIG. 4. There are many optical planes conjugate to 104 that would provide adequate collimation of the beam of light to be controlled, but positioning the light intensity adjustment prior to further optical elements reduces the amount of unwanted scatter in the instrument. A fourth manner of adjustment of the intensity of the illumination light uses electronic control, for example, from the control electronics depicted as 46 in FIG. 2 in communication with the light sources or the intensity control element to adjust power, voltage, or current. A detector gain control can be used as well to increase or decrease contrast.

In an exemplary embodiment using three illumination sources such as shown in FIG. 4, illumination source 86 is a HeNe laser at 543 nm, source 88 is a diode laser at 830 nm, and source 90 is a vertical cavity surface emitting laser (VCSEL) at 850 nm. Diode lasers and VCSELs such as illumination sources 88 and 90 can readily be operated using direct current and can thereby be operated by one or more batteries. Battery operation allows the optical imaging device to be portable and used in remote locations.

In this embodiment, the VCSEL 90 is of unusually small size for an illumination source in an optical imaging instrument, as VCSELs are typically used in communications and optical computing, not optical imaging instruments. The footprint of the device using this source is thus more compact, and the weight is reduced compared to conventional imaging devices. The energy efficiency of the VCSEL 90, being unusually high, as well as the possibility of utilizing direct current such as from a battery, also assists in reducing the weight and footprint of the present imaging device. This diameter of the laser element of a VCSEL can be as small as 50 microns, plus the associated housing and beam shaping elements that are larger; the total package except for the power supply is approximately the size of a small integrated circuit or transistor in a can mount. In this context, the VCSEL is merely one more electronic component in the circuit. The high energy efficiency permits the output to be in the low mW range when using a single battery, such as a 9 V battery plus current limiting circuitry.

Diode laser illumination source 88 is of an intermediate size and provides an intermediate footprint and weight, and also supports the possibility of battery operation and remote use. Any infrared or near infrared source having an appropriate size, energy efficiency, power density, beam quality, and weight can be used as an illumination source to replace the sources described in conjunction with 86, 88, or 90 in FIG. 4.

When the target is the human eye or other substance that remits near infrared or infrared light, the embodiment in FIG. 4 allows the target to be viewed with a safe and (where applicable) comfortable amount of illumination, using illumination sources 88 or 90. A near infrared source is important for penetrating thin blood layers and the lens with cataractous changes. Near infrared sources, when used to image the retina, do not lead to constriction of the human pupil, thereby providing sufficient illumination to use the imaging device in a non-mydriatic manner, with either flashed or steady-state illumination. An illumination source with near-infrared wavelength having a beam of acceptable quality produces an image of acceptable quality when used in a scanning system, such as those depicted in FIG. 2, 3, or 4. The imaging device can be limited to use with a near infrared source for use in an environment of daylight, room light, or other visible wavelength light by positioning a filter blocking the visible wavelength light, using any suitable position, where the light is approximately in a plane optically conjugate with the plane of target 82, such as between the target 82 and a focusing lens 108 in FIG. 4.

The illumination source 86, as depicted in FIG. 4, can be of a shorter wavelength than sources 88 or 90. Examples include but are not limited to HeNe lasers, Argon lasers, solid state lasers such as a frequency doubled YAG laser, and other short wavelength sources such as lamps and light emitting diodes of sufficient power density and beam quality to permit scanning of a slit of uniform intensity across the target, as would be known by those of skill in the art. In the eye and other biological tissues, the use of a shorter wavelength, specifically in the range of 514 to 594 nm, enhances the contrast of structures containing blood, but can lead to constriction of the human pupil. For the detection pathway to utilize a modest cost detector array, it is necessary to use a sufficiently bright source to provide an image despite this constriction. Therefore, the light source of short wavelength can be used in a flashed mode, following alignment of the target and the imaging device using a near infrared illumination source, such as sources 88 or 90 in FIG. 4. An example in the human eye is the detection or management of diabetic retinopathy. Similarly, for reflectance or fluorescence imaging, a light source of one wavelength range can be used for alignment prior to imaging to prevent excessive light exposure, thermal changes, or photobleaching. In the eye three examples are fluorescein angiography and fluorophotometry in the retina and vitreous, and fluorescein staining for tear film quality for the anterior segment.

As noted above, light on the illumination pathway undergoes beam shaping. For example, in FIG. 4, the light from the illumination sources is brought to a focus by cylindrical element 110, so that the power of the sources is concentrated in the shape of a slit, which can be passed through a spatial filter, slit 106, thereby producing a line source. A slit can be formed by either element 110 or 106, but using both elements 110 and 106 improves energy efficiency by coupling more of the light through the slit and directing it towards the target than does, for example, the embodiment depicted in FIG. 3. Light at the slit is in an optical plane conjugate to the plane of the target 82. The slit can be generated by a transmissive or reflective spatial filter, as well as an electronic one, such as a spatial light modulator. After the formation of a slit, the light is directed by a focusing element 112 onto the scanning element 84 so that motion in the direction orthogonal to the long axis of the slit leads to the formation of a raster pattern on the target 82. The light can utilize the same scanning element 84 three times, with the optical plane of three surfaces of 84 being approximately conjugate. For example, the scanning element 84 can be a cube with four reflective surfaces mounted for rotation about a central axis (extending orthogonally to the plane of the figure).

The light directed by the scanning element 84 is then directed by a focusing element 108 and focusing element 114 towards a focus at the target 82. In FIG. 4, the focusing element 114 is movable towards and away from the target 82 under either mechanical or electronic control, similar to a focus adjustment in a conventional camera. The optical plane at the pupil entrance 116 to the target 82 is optically conjugate to the planes of all scanning surfaces, illustrated by scanning element 84. Light remitted by the target 82 is then directed back by the focusing elements 114 and 108 to the scanning element 84, where the beam strikes a portion of the scanning element that is spatially separate from the portion that directs the illumination toward the target 82. The light returning from the target 82 can maintain a spatially separate pathway from that taken when directed toward the target 82, and striking element 84 in a different location, thereby eliminating the need for a separate physical element to provide beam separation of illumination from detection pathways. In another embodiment, there can be a physical beam splitter to separate the illumination and detection pathways, with the constraints that the light returning from the target 82 must be brought to a portion of the scanning element 84 or a scanning element in synchronization with 84 and that the optical plane of all scanning surfaces be conjugate to that of the entrance pupil 116. The second scan returns the beam to a slit configuration to spatially filter the light via a confocal aperture 118 in the detection pathway in a plane optically conjugate to the target 82.

In FIG. 4, the light remitted from the target 82 and reaching a second face of the scanning element 84 is then directed by a series of turning mirrors 120 and 122 to a focusing element 124, followed by additional turning mirrors 126 and 128. The confocal aperture 118 is located on a retinal plane between the turning mirrors 126 and 128. After the turning mirror 128, the light is directed to a focusing element 130 and turning mirrors 132 and 134. The light is then directed to a third face of the scanning element 84. This third scan forms a raster again from the light directed from the slit at the confocal aperture 118 that is directed towards a focusing element 136 and then to the two dimensional detector array 80.

The detector can be a CCD array, a CMOS array, a line scan camera, or other linear or two dimensional electronic detector. A linear array must be placed prior to the third scan, at the location of the confocal aperture 118 or a plane conjugate therewith, or if in a plane conjugate with the pupil, must be in motion in synchronization with the input to the confocal aperture 118. From these individual lines, a raster must then be built. Thus, one or three scans, as embodied by FIG. 3 or 4, respectively represent preferred embodiments until modestly priced line scan cameras or arrays are available. The detector may suitably be of a consumer electronics grade, which reduces expense and weight. The detector is located in the desired focal plane, such as a retinal or subretinal plane, or the vitreous body of the eye. The position of the target plane is manipulated by the movable lenses or other focusing elements, for instance lens 64 in FIGS. 3 and 6, and lens 114 in FIGS. 4 and 7.

In the preferred embodiment for the human retina, the dimensions of the input pupil to the target 82 are small, no more than 2.5 mm in diameter. This permits use of the device in brightly illuminated surroundings or with older people in a remote setting. The size of the target to be imaged, when the human eye is the target, is approximately 6-8 mm, differing from highly magnified experimental instruments but providing a field of view of approximately 20-30° visual angle as in conventional ophthalmic cameras.

As the input and exit pupils are limited to a total of 2 to 2.5 mm, light efficiency is a concern, particularly when the pupil is not dilated. Unlike prior art commercial devices, which scan in two dimensions, the scanning is done in one dimension. The scanning can also be done with two scanning devices, in the manner currently done in commercially available devices, which either oscillate about an axis or rotate 360°, to provide motion of a beam across the back of the eye. An improvement in signal to noise ratio, and therefore image quality, is achieved by reducing the speed of scanning in one or two directions.

A criterion in the design is the preservation of the amount of light reaching the detector from the eye; this is necessary in the light-starved condition of retinal imaging through a small pupil so that the image quality is acceptable. The scanning device can operate slowly near the range of 1-20 Hz, rather than the typical devices used for retinal imaging such as a continuously moving galvonometer or rotating device that operates at 25-60 Hz. This also allows for less power consumption and a mechanically less sophisticated device to be used for scanning. The slow scan can be done such that, when the scanning device is activated by the operator, the scanning can be done with a single or limited number of sweeps across the target.

Some devices may take a portion of the scanning time to get up to speed. To keep the light reaching the detector in the same intensity range, there must be a similar scanning velocity for all points on the target. This can be accomplished by introducing a delay before data are accepted from the detector. In another embodiment, a shutter is provided to prevent the light from reaching the detector until the scanning is at the correct velocity. In a further embodiment, the illumination source is not turned on or its brightness is not increased until the scanning component can produce a sufficiently even and fast speed across the target.

In another embodiment using a limited number of scans, reduced resolution is used during one or more frames to assist with light level, target positioning, and focusing using faster data acquisition, and then higher resolution is used for one or more good quality still frames. Many two dimensional arrays used in consumer electronics now permit operation in more than one mode, still or video; similarly, detector arrays offer more than one resolution. Thus, scanning and acquisition speed, light level, and gain can be traded off against resolution.

The small pupil size and small device size impose constraints on the field of view, which is most likely to be approximately 20° with optical resolution that supports a digital resolution of approximately 512×512 or 640×480 pixels. A large depth of field is preferred. The instrument has intentionally limited confocal sectioning capabilities. This reduces the need for a large input beam at the pupil. The reduction of out of focus light minimizes artifact from anterior segment optics. An aperture in the plane confocal to the retinal plane is used. Additional polarization optics may be used. Another way to provide sufficiently long path lengths, large depth of field, and good image quality is to use a telescoping frame. The path lengths can be extended by mirrors on or near the exterior portions of the frame that are moved, or on another movable component. The present instrument avoids a disadvantage in many prior art designs of having a high f-number final lens in a position such that the pupil plane reflection is sampled in the retinal plane, which results in a bright, unwanted reflection in the image of the retina.

In the present invention, the focusing mechanism is preferably kept simple to minimize complexity of use, size, and weight. Focusing is achieved by increasing or decreasing the relation of retinal and pupil planes (the desired focal plane and the entrance plane) by the use of one or more movable mirrors and/or lenses, such as 114 or 108 in FIG. 4. These components are easily operable by either mechanical or electrical control. In one embodiment, a movable lens or lens array is provided, such as used on modern cameras. The moving mirror or lens can be operated manually by, for example, a rotating knob operated by a single finger or thumb. It can also be operated by grasping a rotable lens housing, in a manner similar to a camera. It can be operated by a slide switch, or any other simple mechanical positioning device. It can be motorized, preferably using a battery-powered DC motor. An AC motor can be used if there is a connection to an external AC power supply.

The proper focus can be found through visualization by a user of images on a display. The focus can also be found by using an indicator to locate the brightest reflection returning from the target, without necessarily having to provide visualization of the data. The focus can be found by using lower resolution images, or a small number of images acquired more rapidly, up to video rate, to find the focus quickly, after which an image having a better resolution is provided. The focus can be a manual mechanism or an autofocus mechanism. The focus can be determined based on all or a portion of the image.

The device may include a display on which the user can see the image, such as a liquid crystal display (LCD). However, because an onboard LCD adds weight, may be fragile, and draws current, it may be desirable in some embodiments to eliminate a display and provide only a focus indicator. As noted above, when the retina is in focus, this layer provides the greatest light return throughout the visible spectrum and near infrared. An image, then, needs only to be positioned on the anterior segment properly to decrease this signal, and the focal plane to sample the retina adjusted to the maximum brightness. Thus, while an image is useful for focusing, with a large depth of field, an indicator also is suitable. The indicator may be a display, a light when a criterion is reached, a light that gets brighter or dimmer corresponding to the amount of light received, a dial, a digital read-out panel, a sound, a needle display, or any other element that can provide a signal to the user that focus has been obtained.

The device may include a display for viewing the image after its acquisition. The display may be a liquid crystal display (LCD) or other suitable display device. The image data may be transferred by USB, IEEE1394, or other connection to a device or computer. The device can include one or more onboard memory devices, either in the integrated circuits or a removable memory device or film that can be transferred to an external viewing device such as indicated at 44 in FIG. 2. The data may be transmitted by either wire or wireless methods to a receiving device, such as a computer, personal desk assistant, cell phone, or other device.

Figure 6:
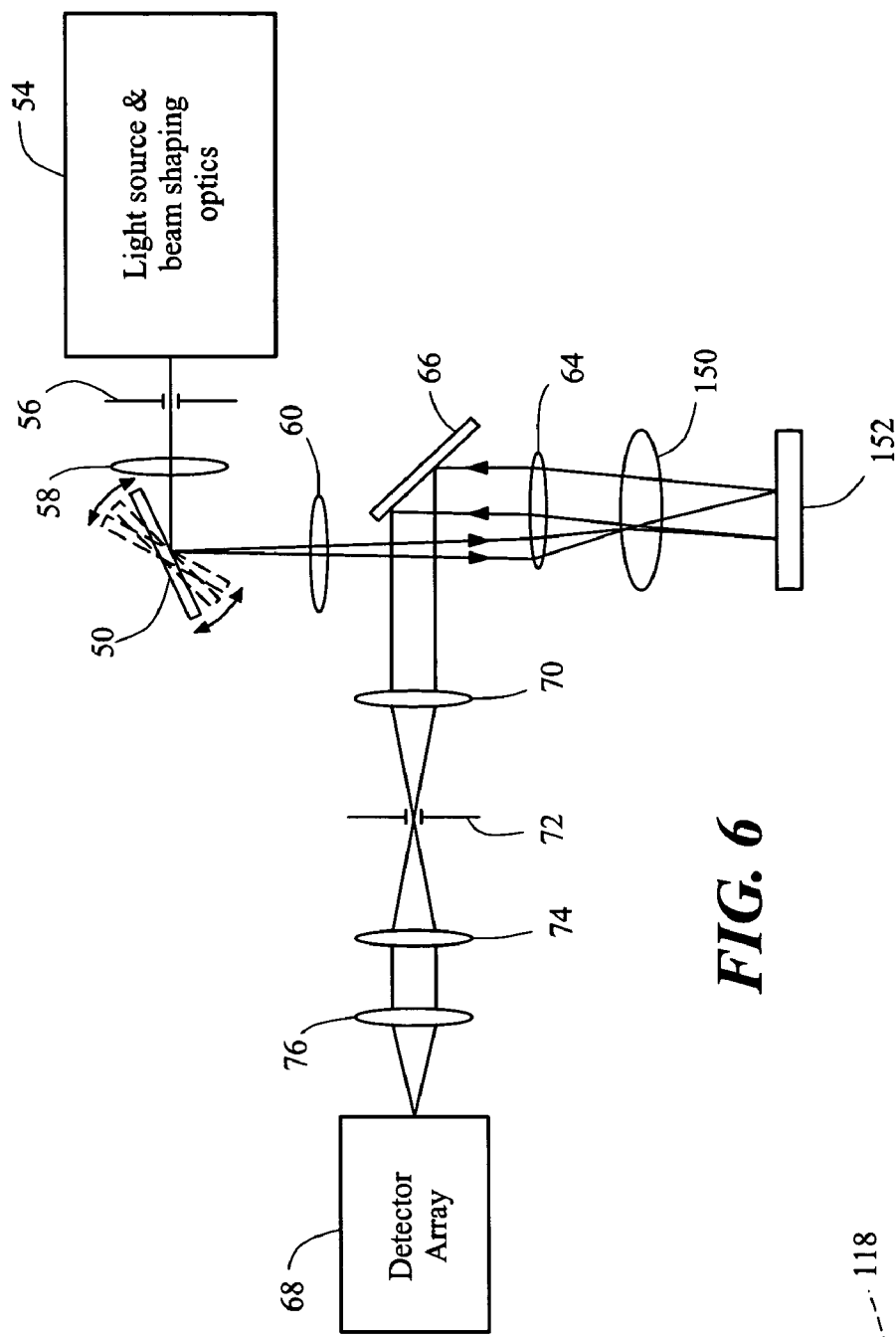
FIG. 6 is a schematic diagram illustrating an embodiment of the optical imaging system incorporating one scanning element, plus an additional focusing element over that of FIG. 3 to allow imaging of a target that does not have a lens.
Figure 7:
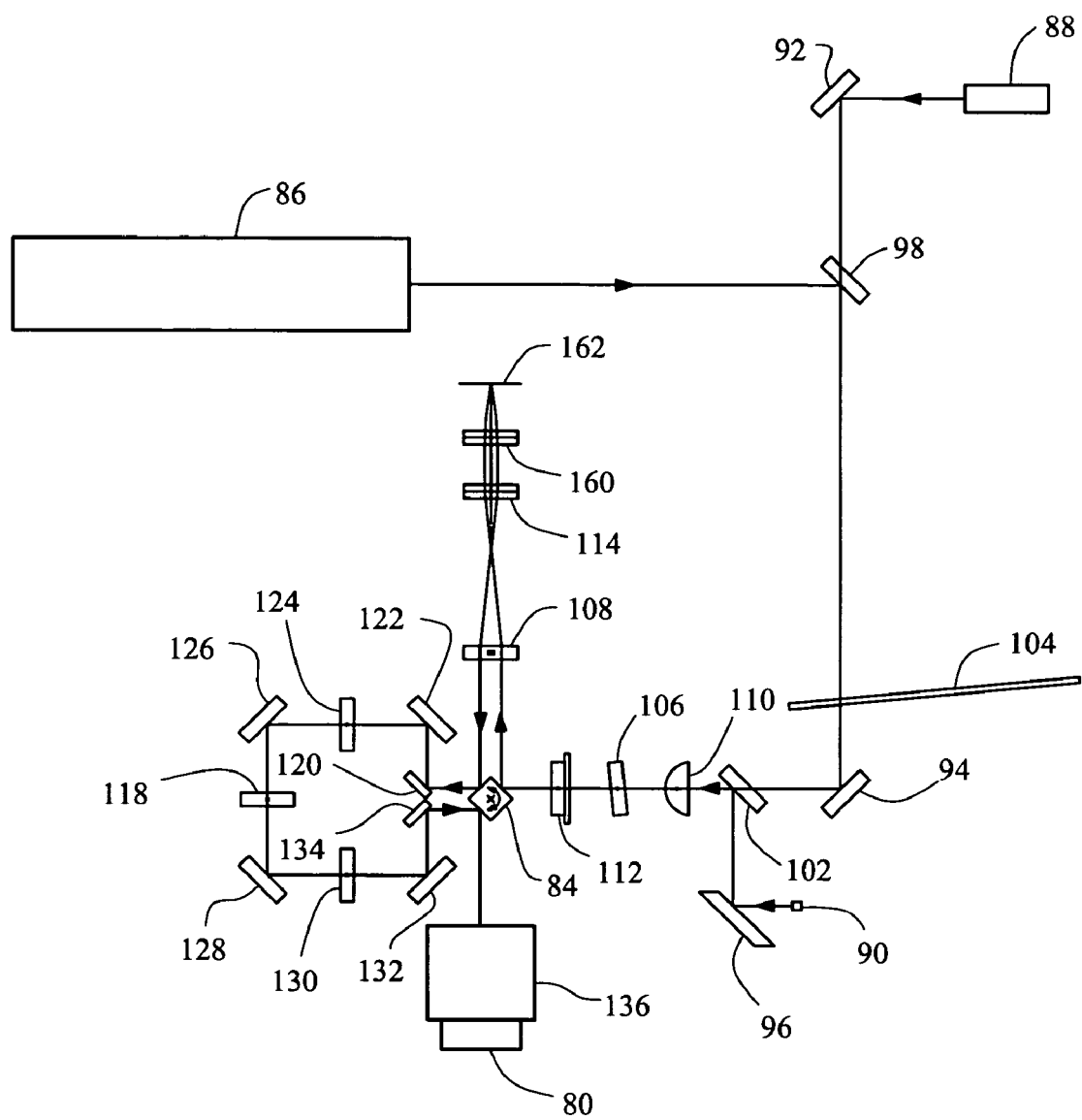
FIG. 7 is a schematic diagram illustrating an embodiment of the optical imaging system of the present invention incorporating one scanning elements and three instances of scanning utilizing three portions of the element, plus an additional focusing element over that of FIG. 4 to allow imaging of a target that does not have a lens.

To view structures in a plane not conjugate to the retina of the eye, that is structures that do not lie behind a focusing unit such as the lens of the eye, modifications may be made to what is essentially a focusing assembly shown by lenses 60 and 64 in FIG. 3 and 108 and 114 in FIG. 4. A further lens or mirror assembly may be added, existing lens or mirrors removed, or other lenses or mirrors substituted for the focusing assembly. FIG. 6 illustrates adding an additional lens element 150, which can be movable, to the embodiment shown in FIG. 3 to bring a target 152 into focus. FIG. 7 illustrates adding an additional lens 160, which can be movable, to the embodiment shown in FIG. 4 to bring a target 162 into focus. These structures include the anterior segment of the eye, but are not limited to ocular structures and could include skin or any other biological or non-biological structure. The narrow entrance pupil and the separation of illumination and detection pathways distinguish this design from an optical confocal microscope device intended for optical sectioning with the highest axial resolution, although the embodiments shown in FIGS. 3 and 4 allow for an instrument with some optical sectioning capability, i.e. an instrument that could be used as a microscope or general purpose imaging device of modest resolution and rejection of out of plane remitted light. The focusing elements as shown can be used to provide an image that enlarges the view of a target, and further enlargement of an image for viewing occurs largely electronically, thus broadening the potential uses beyond that of the human retina or eye as a whole. Further, the scanning of the illumination source with respect to the target provides an image of higher contrast than does typical flood illumination or illumination from existing and external sources such as daylight, and in this way broadens the potential uses of the device beyond the scope of the human retina or eye.

For the anterior segment of the human eye, structure imaged by using the ancillary or substituted focusing elements that are not in the focal range of the digital retinal imaging device are many. The device could be used to image corneal trauma or disease, results from corneal surgery or refractive laser surgery, foreign body, chemical injury or burn, iris neovascularization, exterior ocular injuries, burns, contact lens fit, external inflammation, infectious disease, tear duct problems, lid lesions, pterigeum, scleral or iris vessel problems, or other data needed to document the emergency or health status of a patient.

Figure 8:
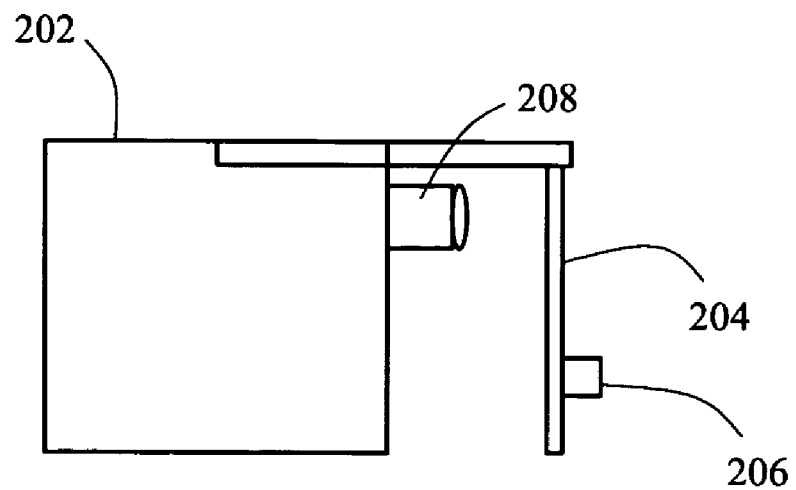
FIG. 8 is a schematic diagram illustrating a casing for the device having a telescoping or foldable head or chin rest and an eyepiece.
Figure 9:
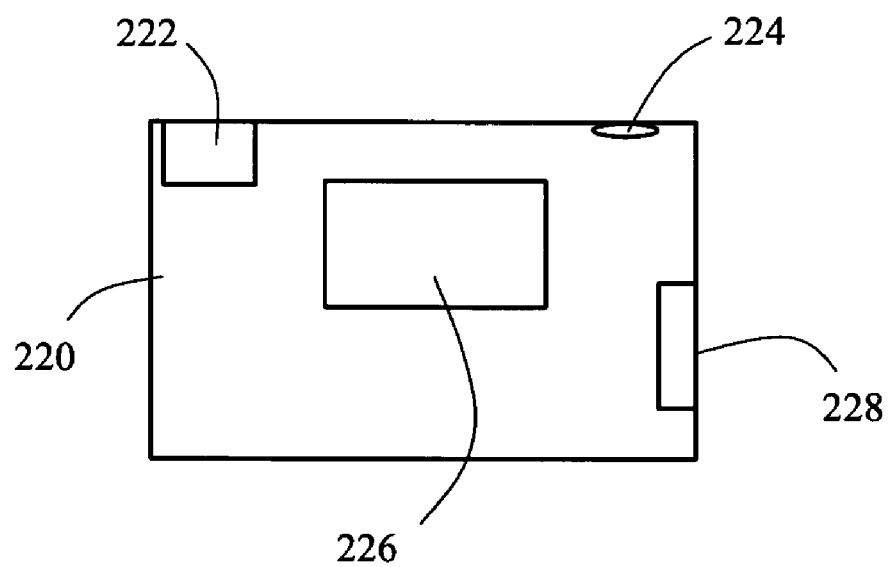
FIG. 9 is a schematic diagram illustrating a casing for the device, showing a single button control, an LCD display, a view finder for locating the eye, and a port for locating the data transfer media or connectors.

The above-described components of the present optical imaging device are housed in a suitable casing. Controls, such as an on-off switch and a focusing control, are accessible through the casing to the user. A head or chin rest can be provided, configured to allow a patient to hold the eye in a steady manner in alignment with the device. FIGS. 8 and 9 illustrate two examples of such a casing. FIG. 8 illustrates a device in a casing 202. The casing is rugged and lightweight and encloses all the optical and electronic components described above. A head or chin rest 204 with an adjustable chin piece 206 is provided to align the subject's eye or target to an eyepiece 208. The head or chin rest can be telescoped to form a readily packed and carried portable device. In another embodiment, the head or chin rest can be folded to form a compact footprint. FIG. 9 illustrates a further embodiment having a casing 220 that is held by the user in a manner similar to a consumer digital camera. A viewfinder 222 is provided for locating the eye. A single button control 224 on the casing can act as a toggle switch for off and on and for various modes or resolution of image acquisition. An LCD display 226 is provided, on which images and operational information can be provided. A port 228 is provided for locating the data transfer media or connectors.

A number of embodiments of the present device have been built and tested to determine the feasibility of obtaining acceptable eye images safely and under battery power with the capability of transferring images to a remote source. A number of embodiments were tested using a model human eye, as known in the art. The model eye was used to determine that the device is able to operate and obtain an image using an acceptable amount of light that is consistent with eye safety. The relative amount of light in the model eye has been calibrated to the human eye and is known.

An embodiment similar to that described in conjunction with FIG. 4 was built and operated using only battery power for the light source, the motor to operate the scanning element, and the detector. For each of these three elements, a 9 V battery was used. This device was also connected to a computer, which included its own source of battery power, and images were transferred to the computer.

An embodiment similar to that described above in conjunction with FIG. 4 was built and tested on a human eye, after obtaining required regulatory approval. Suitable images of the retinal plane of a human eye were obtained at an appropriate resolution, having good contrast, and with no strong reflections from the corneal planes. Features known to be unique to the particular human eye tested were recognizable.

This invention is particularly applicable within the fields of ophthalmology, optometry, emergency services, military ocular screening, ocular screening in any mass situation, health care workers providing diagnoses at locations remote from eye care specialists, telemedicine, and eye examination by persons without specialty eye care skills, such as pediatricians, ER technicians, or family practitioners. A primary application of the device is for use by, for example, emergency personnel, when there is a suspicion of trauma to the eye. In such situations, it can be helpful to know if an individual with a suspected eye injury can be allowed merely to rest for a period of time or if, instead, the patient requires further emergency treatment. A further application is the remote or mass screening for potential eye disease by personnel who are not primarily specialists in the eye, such as pediatricians or family practitioners. The device has a minimum of controls, which provides simplicity in operation, so that a high degree of training is not required to operate the device.

In contrast to the present invention, current commercially available scanning laser ophthalmoscopes are too large and expensive for use as a portable device in the field. Further, these devices are complex and require a user to be highly trained both in using the device and in reading the resulting ophthalmic images. The striking image quality of the large SLOs and the sectioning capabilities of tomographic devices, which spoil the signal to noise ratio, are not needed in the present device.

The description above pertains to several illustrative embodiments of the invention. Many variations of the invention may be envisioned by one skilled in the art. Accordingly, such variations and improvements are intended to fall within the compass of this disclosure. The invention is not to be limited by what has been particularly shown and described, except as indicated by the appended claims.

What is claimed is:

1. An imaging device for the eye comprising:
   an illumination source;
   a scanning arrangement disposed on an illumination path from the illumination source to a target, the scanning arrangement operative to scan light passed through a slit in front of the target in the illumination path across a desired focal plane of the target through an entrance more narrow than the desired focal plane;
   a detection arrangement disposed to receive light remitted from the target and operative to produce an image;
   a beam separation arrangement disposed on a return path from the target separated from the illumination path, the beam separation arrangement operative to receive light remitted from the target and to direct remitted light on a detection path to the detection arrangement; and
   a controller in communication with the illumination source, the scanning arrangement, and the detection arrangement.

2. The device of claim 1, wherein the focal plane of the target comprises a plane in the retina or tissues beneath the retina of the eye.

3. The device of claim 1, wherein the entrance comprises the pupil of the eye.

4. The device of claim 1, wherein the beam separation arrangement is configured to space the illumination path and the return path sufficiently apart to reduce reflections from sources out of the desired focal plane and sufficiently closely to obtain an image of a sufficient desired resolution.

5. The device of claim 1, wherein the beam separation arrangement is configured to space the illumination path and the return path sufficiently apart to reduce reflections from sources out of the desired focal plane and sufficiently closely to obtain returned light through a central region of the pupil having a diameter of 2 mm.

6. The device of claim 1, wherein the scanning arrangement and the detection arrangement are configured to provide an image resolution sufficient to match an image of 1 megapixel or less.

7. The device of claim 1, further comprising an optical assembly configured to form light on the illumination path into a slit in a plane conjugate to the desired focal plane of the target.

8. The device of claim 1, further comprising an optical assembly configured to focus light at the slit in the illumination path in a plane conjugate to the desired focal plane of the target.

9. The device of claim 1, wherein the scanning arrangement further comprises a rotating reflective element.

10. The device of claim 1, wherein the scanning arrangement further comprises an oscillating reflective element.

11. The device of claim 1, wherein the scanning arrangement is operative to scan at a frequency less than 20 Hz.

12. The device of claim 1, wherein the scanning arrangement further comprises a reflective scanning element located in a plane conjugate to a plane of the entrance.

13. The device of claim 1, further comprising an optical assembly configured to focus light on the illumination path from the scanning arrangement on the desired focal plane of the target.

14. The device of claim 13, wherein the optical assembly is adjustable to adjust the focus.

15. The device of claim 13, further comprising an additional focusing element configured to focus on a target that does not fall behind a lens.

16. The device of claim 1, wherein the beam separation arrangement further comprises a reflective or transmissive surface.

17. The device of claim 1, wherein the beam separation arrangement further comprises a beam splitting device.

18. The device of claim 1, wherein the beam separation arrangement further comprises a polarizing beam splitting device.

19. The device of claim 1, wherein the beam separation arrangement is configured to minimize reflections from focal planes not in the desired focal plane of the target from reaching the detection arrangement.

20. The device of claim 1, wherein the beam separation arrangement further comprises a reflective or transmissive element spaced off the illumination path.

21. The device of claim 1, wherein the beam separation arrangement further comprises an aperture located in an optical plane conjugate to the desired focal plane of the target, the aperture configured to minimize reflections from focal planes not in the desired focal plane of the target from reaching the detection arrangement.

22. The device of claim 1, wherein the detection arrangement includes an image acquisition element located in a plane conjugate to the desired focal plane.

23. The device of claim 1, wherein the detection arrangement includes a digital arrangement for image acquisition or display.

24. The device of claim 1, wherein the detection arrangement includes a CCD device for image acquisition or display.

25. The device of claim 1, wherein the detection arrangement includes a CMOS device for image acquisition or display.

26. The device of claim 1, wherein the detection arrangement includes a video camera for image acquisition or display.

27. The device of claim 1, wherein the detection arrangement includes an element operative to convert light energy into electronic or magnetic energy for image acquisition or display.

28. The device of claim 1, wherein the detection arrangement includes a display for viewing an image.

29. The device of claim 28, wherein the display comprises a liquid crystal display.

30. The device of claim 1, wherein the detection arrangement is operative to produce a monochrome image.

31. The device of claim 1, wherein the detection arrangement is operative to produce a monochrome image having a contrast sufficient to be displayed on a device without color.

32. The device of claim 1, wherein the illumination source comprises a near infrared source.

33. The device of claim 1, wherein the illumination source comprises an infrared source.

34. The device of claim 1, wherein the illumination source comprises a HeNe laser, an argon laser, or a frequency doubled YAG laser.

35. The device of claim 1, wherein the illumination source comprises a diode laser, a vertical cavity surface emitting laser, a light emitting diode, or a lamp.

36. The device of claim 1, wherein the illumination source comprises light from a plurality of light sources combined onto the illumination path.

37. The device of claim 1, further comprising a light intensity controlling element located in the illumination path.

38. The device of claim 37, wherein the light intensity controlling element comprises an optical element, a mechanical element, a polarizing element, or an electronic element in communication with the illumination source and the controller.

39. The device of claim 37, wherein the light intensity controlling element comprises a neutral density filter.

40. The device of claim 1, wherein the controller is operative to control the illumination source to provide flashes of illumination.

41. The device of claim 1, wherein the illumination source is operative to provide continuous illumination.

42. The device of claim 1, further comprising an additional scanning arrangement disposed on the return path and operative to scan light passed through an aperture in the return path across a detection element in the detection arrangement.

43. The device of claim 1, wherein the detection element lies in a plane conjugate to a plane of the entrance.

44. The device of claim 1, further comprising a DC power source in communication with the illumination source, the scanning arrangement, the detection arrangement, and the controller.

45. The device of claim 44, wherein the DC power source comprises at least one battery.

46. The device of claim 1, wherein the scanning arrangement includes a motor.

47. The device of claim 1, wherein the motor comprises a DC motor.

48. The device of claim 1, further comprising an output element operative to transmit an image from the detection arrangement to an external device.

49. The device of claim 48, wherein the output element comprises a cable port or a wireless broadcast device.

50. The device of claim 1, further comprising a head or chin rest configured to fix a position of the eye relative to the scanning arrangement.

51. The device of claim 1, wherein the device is sufficiently small to be hand held.

52. The device of claim 1, further comprising a database comprising images obtained from the device.

53. The device of claim 52, wherein the database is sized to store 10 or fewer images per patient, each image of 1 megapixel or less.

54. The device of claim 1, further comprising a database of images to train a user to operate the device.

55. A method of using the device of claim 1, comprising: positioning the device adjacent an eye to be imaged; and operating the device to obtain an image.

56. The method of claim 55, wherein the device is operated to obtain an image under battery power.

57. The method of claim 55, wherein the device is operated to obtain an image without communication with an AC power source.

58. The method of claim 55, further comprising transmitting an obtained image to a remote location.

59. The method of claim 58, wherein the image is transmitted to the remote location via cable or wireless transmission.

60. The method of claim 55, further comprising attaching a computer to the device and transmitting an obtained image to the computer.

61. The method of claim 55, further comprising attaching a personal digital assistant to the device and transmitting an obtained image to the personal digital assistant.

62. The method of claim 61, wherein the image transmitted to the personal digital assistant is sized to allow viewing on the personal digital assistant with a minimum amount of scrolling.

63. The method of claim 55, wherein the image is obtained without use of mydriatic medication to dilate the pupil of the eye.

64. The method of claim 55, wherein the image is obtained under daylight conditions.

65. The method of claim 55, wherein the image is obtained under room light conditions.

66. The method of claim 55, wherein the device is operated to obtain an image of the retina of the eye.

67. The method of claim 55, wherein the device is operated to obtain an image of the anterior segment of the eye.

68. The method of claim 55, further comprising training a user to operate the device using a database of images.

69. The method of claim 68, wherein the user is trained onsite to determine an outcome based on results from the device.

70. The method of claim 55, further comprising training a user located remotely from the device to determine an outcome based on results from the device.

71. The method of claim 55, wherein the device is operated to obtain an image in a cordless mode.

72. The method of claim 70, wherein the remotely located user is operating another computer or personal digital assistant.

73. The method of using the device of claim 1, comprising:
using the device to obtain an image of a retina or tissues beneath the retina of the eye, utilizing high contrast achieved by scanning and modest light levels sufficient for image formation.

74. The method of using the device of claim 1, comprising:
using the device to obtain an image of the anterior segment of the eye, utilizing high contrast achieved by scanning and modest light levels sufficient for image formation.

75. A method of using the device of claim 1, comprising:
using the device to obtain an image of a target, utilizing high contrast achieved by scanning and modest light levels sufficient for image formation.

76. A method of using the device of claim 1, comprising:
using the device to obtain an image of a target, utilizing magnification achieved by use of a display, along with high contrast achieved by scanning and utilizing modest light levels sufficient for image formation.

77. A method of using the device of claim 1, further comprising:
using the device to obtain images;
storing the images in a database;
training a user with the images to operate the device with or without expert assistance.

78. A method of using the device of claim 1, further comprising:
using the device to obtain images;
storing the images in a database;
training a user with the images to determine an outcome based on the results from the device with or without expert assistance.

79. The method of claim 78, wherein the user is trained on site using the device.

80. The method of claim 78, further comprising transmitting the images to a remote site and training the user at the remote site.

81. The device of claim 1, wherein the device is operative in a cordless mode.

82. A method for obtaining an image of an eye, comprising:
forming light from an illumination into a slit in an optical plane conjugate to a target;
scanning the formed light across the target plane in an eye;
separating light returning from the eye from light entering the eye sufficiently apart to reduce reflections from sources out of the target plane and sufficiently closely to obtain a desired sufficient image resolution;
detecting light from the target plane; and
forming an image from the detected light.

* * * * *